(12) United States Patent
Walsh, IV et al.

(10) Patent No.: US 10,524,967 B2
(45) Date of Patent: Jan. 7, 2020

(54) ORTHOPEDIC CAST REMOVAL APPARATUS

(71) Applicant: RhinoX Tool, LLC, Columbia, SC (US)

(72) Inventors: John Joseph Walsh, IV, Columbia, SC (US); Boyce Lee Muller, Columbia, SC (US)

(73) Assignee: RhinoX Tool, LLC, Columbia, SC (US)

( * ) Notice: Subject to any disclaimer, the term of this patent is extended or adjusted under 35 U.S.C. 154(b) by 34 days.

(21) Appl. No.: 15/412,910

(22) Filed: Jan. 23, 2017

(65) Prior Publication Data

US 2017/0209317 A1     Jul. 27, 2017

Related U.S. Application Data

(60) Provisional application No. 62/286,048, filed on Jan. 22, 2016.

(51) Int. Cl.
*A61F 15/02*     (2006.01)
*B23Q 11/00*     (2006.01)
*B23D 61/00*     (2006.01)

(52) U.S. Cl.
CPC .................................. *A61F 15/02* (2013.01)

(58) Field of Classification Search
CPC ........................................................ A61F 15/02
See application file for complete search history.

(56) References Cited

U.S. PATENT DOCUMENTS

| | | | |
|---|---|---|---|
| 1,530,023 A | 3/1925 | Walton | |
| 2,490,878 A | 12/1949 | Marsh | |
| 2,492,156 A * | 12/1949 | Kupjack | A61F 15/02 30/370 |
| 3,103,069 A | 9/1963 | Gary | |
| 3,214,869 A | 11/1965 | Stryker | |
| 3,606,681 A * | 9/1971 | Rogers | B26B 13/24 30/133 |
| 4,421,111 A | 12/1983 | Rothman | |

(Continued)

FOREIGN PATENT DOCUMENTS

WO    2010120322 A1    10/2010

OTHER PUBLICATIONS

International Search Report and Written Opinion dated Apr. 20, 2017 in corresponding international application serial No. PCT/US2017/014586, all enclosed pages cited.

*Primary Examiner* — Stephen Choi

(74) *Attorney, Agent, or Firm* — Nelson Mullins Riley & Scarborough, LLP

(57) ABSTRACT

An orthopedic cast removal apparatus comprises a housing having a portion that can be gripped by an operator during use. A motor is located inside the housing. A blade is operatively connected to and driven by the motor via a drive mechanism, the blade defining a cutting edge having cutting teeth located thereon. The drive mechanism according to this aspect has a driven element with an axis of rotation substantially parallel to a surface of an orthopedic cast when it is cut. The blade is connected to the driven element at a connection point that moves periodically around the axis of rotation. As a result, the cutting edge of the blade engages material of the orthopedic cast in a galloping fashion.

11 Claims, 3 Drawing Sheets

(56) References Cited

U.S. PATENT DOCUMENTS

| | | | | |
|---|---|---|---|---|
| 4,625,405 A | * | 12/1986 | Hudnutt | A61F 15/02 30/370 |
| 5,115,567 A | | 5/1992 | Yang et al. | |
| 5,435,066 A | * | 7/1995 | Bare | A61F 15/02 30/388 |
| 5,964,039 A | | 10/1999 | Mizoguchi et al. | |
| 6,219,922 B1 | | 4/2001 | Campbell et al. | |
| 6,543,549 B1 | | 4/2003 | Riedl et al. | |
| 6,782,781 B2 | * | 8/2004 | Rack | B23D 61/126 30/392 |
| 8,672,943 B2 | | 3/2014 | Fisher et al. | |
| 2007/0282344 A1 | * | 12/2007 | Yedlicka | A61B 17/1615 606/80 |
| 2009/0205210 A1 | | 8/2009 | Artmeier et al. | |

* cited by examiner

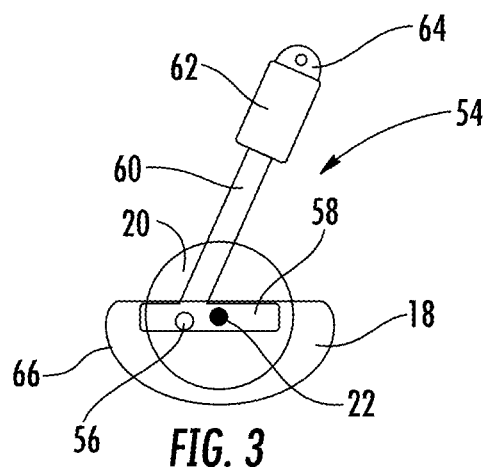
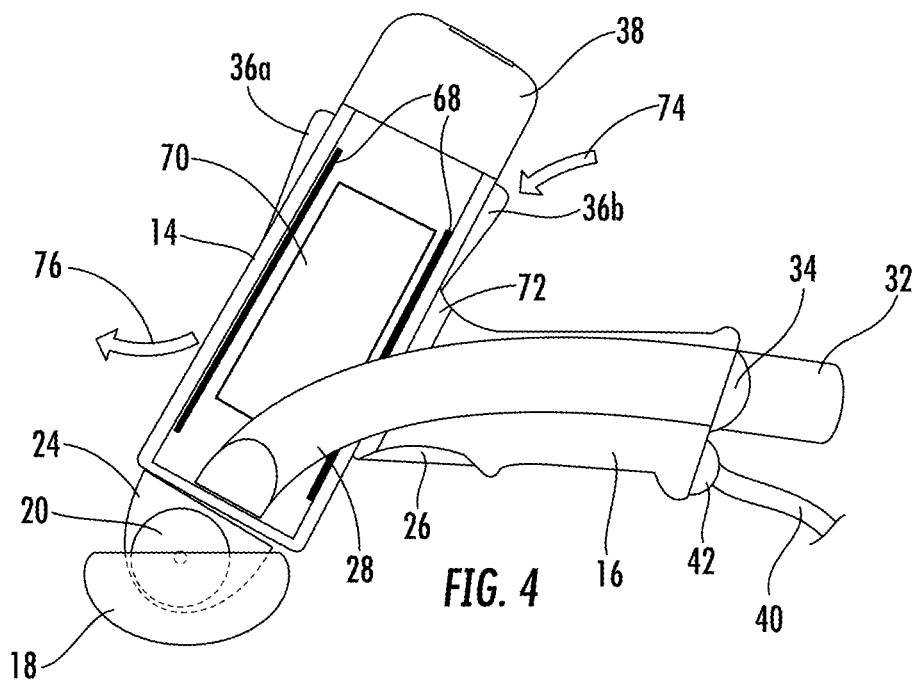

ORTHOPEDIC CAST REMOVAL APPARATUS

PRIORITY CLAIM

This application is based upon and claims the benefit of U.S. provisional patent application Ser. No. 62/286,048, filed Jan. 22, 2016, which is incorporated by reference herein in its entirety for all purposes.

FIELD OF THE INVENTION

The present invention relates to orthopedic cast saws used to remove a cast from a patient.

BACKGROUND OF THE INVENTION

Casts made of a variety of materials and thicknesses are often used to facilitate healing of injuries in human and animal patients. For example, casts may be formed of plaster or fiberglass cloth over cotton gauze. At a certain point in the healing process, the cast will be removed by a medical practitioner, often using a cast saw.

Known cast saws are evolved from cadaver saws and woodworking tools, with little change to these two designs. The first group of tools employs a blade mounted on a shaft which runs longitudinally through the tool and the location where the tool is gripped by the operator's hand, and cuts at a right angle to this shaft. The motor and most weight is aft of the hand, and the operator must move the tool left and right. The operator's wrist and thumb are used to move constantly the blade in and out of the cast material being cut.

The second group of tools has the motor located within the area gripped by the operator's hand. This provides better balance, but the diameter of the device is larger which is a problem for operators with small hands. This type of tool uses a right angle gear box to mount the blade in line with the tool body, so the cutting motion is to push the tool into the cast material. Because the tool is held free in the air, it cannot be easily controlled or stabilized on the cast, and must be moved with constant wrist motion.

Both of these tools oscillate the blade in a narrow arc of about 2.5 to 3.0 degrees and use small teeth to avoid enough motion to cut the patient should the blade come into contact with the skin. This small motion of the blade is further reduced by the reaction of the tool to the blade motion and counter-oscillation of the tool body. This means that only a few of the teeth are actually engaging the cast material on any stroke, so the stroke is less than optimum. The high oscillation speed of the tool (approximately 15,000 per minute) is translated into vibration of the tool in the operator's hand and a loud noise is produced. The blade teeth fill with dust and cease to cut, so the operator must move the blade in and out of the work constantly to put clean teeth into the cast cut. This inefficiency of the cutting motion, combined with the gear box and oscillating mechanism, requires more power yielding more heat and more noise. The power requirements are too much for many battery powered motors, so AC motors are used. AC motors are powerful, but are noisy (e.g., due to the brushes).

Overall, cast saws of the prior art are heavy and tiring to use. Many medical personnel simply cannot handle them. They are noisy to point of being detrimental to hearing, so many of them have to be used in special rooms. Their vacuum systems are also noisy, and must be isolated in closets. Example cast saws of the prior art are shown and described in U.S. Pat. No. 1,530,023, issued Mar. 17, 1925 to Walton, U.S. Pat. No. 2,490,878, issued Dec. 13, 1949 to Marsh, and U.S. Pat. No. 3,103,069, issued Sep. 10, 1963 to Gary. Each of the foregoing patents is incorporated herein by reference in its entirety for all purposes.

SUMMARY OF THE INVENTION

The present invention recognizes and addresses the foregoing considerations, and others, of prior art construction and methods.

One aspect of the present invention provides an orthopedic cast removal apparatus comprising a housing having a portion that can be gripped by an operator during use. A motor is located inside the housing. A blade is operatively connected to and driven by the motor via a drive mechanism, the blade defining a cutting edge having cutting teeth located thereon. The drive mechanism according to this aspect has a driven element with an axis of rotation substantially parallel to a surface of an orthopedic cast when it is cut. The blade is connected to the driven element at a connection point that moves periodically around the axis of rotation. As a result, the cutting edge of the blade engages material of the orthopedic cast in a galloping fashion.

In some exemplary embodiments, the connection point may orbit around the axis of rotation in a circular path. The drive mechanism may often include a right angle gearbox interconnecting an output shaft of the motor with the driven element. Moreover, the driven element may be part of a slider crank mechanism. For example, the driven element may comprise a blade mounting bar integrally attached to a slider bar. In such embodiments, the slider bar may slidably move in a slider housing pivotally attached to the housing of the cast removal apparatus.

Often, the housing may be configured having a main housing portion containing the motor and a grip portion attached to the main housing portion. In such embodiments, the blade may be oriented in a plane that is parallel to an axial plane of the grip portion. A sound absorbing material may be advantageously located inside the main housing portion.

Further embodiments may be provided in which a vacuum duct passes through the housing. In such embodiments, a vacuum inlet will be defined in the housing in fluid communication with the vacuum duct. A vacuum outlet is defined in the housing for connection to an external vacuum source, such as via a swivel connection.

In some embodiments, a foot may be mounted to the housing to limit the plunge depth of the blade. The motor in some embodiments may comprises a DC motor powered by at least one battery pack received in a receptacle defined in the housing. Alternatively, the motor may comprise an AC motor.

Embodiments are contemplated in which a cutting edge of the blade has a generally semicircular configuration. Alternatively, the cutting edge of the blade may have a forward edge portion, an aft edge portion, and a concave bottom edge portion.

Another aspect of the present invention provides apparatus comprising a housing having a main housing portion and a grip portion attached to the main housing portion. A motor is located inside the main housing portion. A blade is operatively connected to and driven by the motor via a drive mechanism, the blade defining a cutting edge having cutting teeth located thereon. Further, the blade is oriented in a plane that is parallel to an axial plane of the grip portion. The drive mechanism is operative to move the blade in a periodic galloping motion so that the cutting edge of the blade will engage material to be cut.

A still further aspect of the present invention provides a blade for use with an orthopedic cast removal apparatus. The blade comprises a generally flat blade member having a generally rectangular shape defining a peripheral edge having a forward edge portion, an aft edge portion, a top edge portion, and a bottom edge portion. A plurality of cutting teeth are located on at least the forward edge portion, the bottom edge portion, and the aft edge portion. Moreover, the bottom edge portion may have a concave recess shape in some preferred embodiments.

The accompanying drawings, which are incorporated in and constitute a part of this specification, illustrate one or more embodiments of the present invention.

BRIEF DESCRIPTION OF THE DRAWINGS

A full and enabling disclosure of the present invention, including the best mode thereof directed to one of ordinary skill in the art, is set forth in the specification, which makes reference to the appended drawings, in which:

FIG. 3 diagrammatically illustrates an example drive mechanism for moving the blade of the apparatus of FIG. 1.

FIG. 4 is a diagrammatic sectional view somewhat similar to FIG. 1 but showing certain details internal to the housing.

Figure 1:
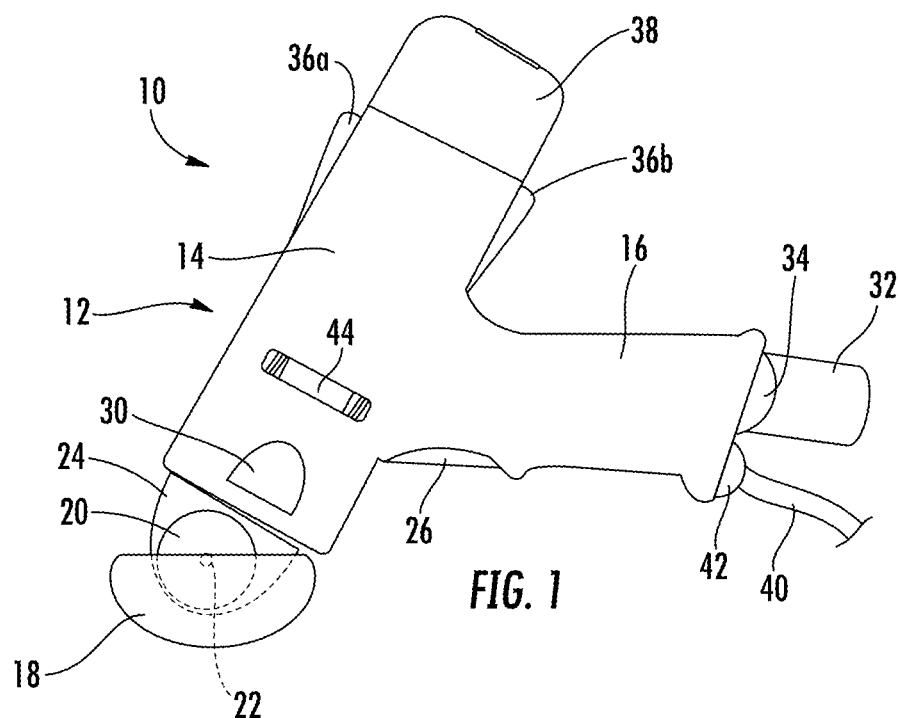
FIG. 1 is a diagrammatic side elevational view of a cast removal apparatus constructed in accordance with an embodiment of the present invention.

Repeat use of reference characters in the present specification and drawings is intended to represent same or analogous features or elements of the invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

Embodiments of the present invention employ a unique cutting motion and a drive mechanism for it, which are more efficient and cut faster while requiring less power (and thus less weight) than prior art cast saws. Preferably, modern materials are combined to reduce weight, noise, and vibration, to the benefit of the operator and the patient. Preferred embodiments employ a modular design, and can be adapted for either battery operation (e.g., using a DC motor) or corded mains source operation (e.g., using an AC motor). The cutting motion and blade design reduces dust, and an integrated vacuum attachment carries dust away from the patient and operator for collection. The blade can be thinner than those of the prior art, thereby removing less material width and requiring less energy to cut the same linear distance with more control.

In this regard, preferred embodiments cut on a pulling stroke, rather than oscillation. This stroke is much longer, so more teeth engage and remove more material on each stroke. Rather than the blade oscillating about a shaft, some preferred embodiments of the present invention utilize a slider crank mechanism. For example, the motor may turn a wheel through a right angle gear box. The blade itself be mounted at a "T" end of a slider crank which is driven by the wheel. The saw blade motion can be adjusted by how it is mounted on this slider. The profile of the blade and the drive mechanism preferably produce an orbital or elliptical motion which gradually enters the teeth into the cast material, with each following tooth entering a little deeper. All the engaging teeth will preferably exit the material on each stroke, which helps clear dust from the teeth.

A drive mechanism of the present invention increases torque rather than losing torque. As a result, the cast saw can operate at a lower speed than the prior art, while still putting many more teeth into the cast material per second. This results in less vibration, less noise, and lower power requirements. The narrow kerf cut into the material results in less dust than would otherwise be the case.

An adjustable and removable foot may be provided to stabilize the cast removal apparatus so that more cutting power can be delivered to the material. Preferably, the foot is also configured to allow a quick and precise adjustment of plunge depth. Unlike prior art, this tool can be set so that the blade cannot come into contact with the patient's skin.

The main housing of the cast removal apparatus may have a suitable bracket or the like to allow removable attachment of a blade housing. The blade housing may be formed, for example, from clear plastic material so that the blade inside can be seen by the operator during use. This blade housing (or cover) provides more protection for the patient, and can serve to push skin away in a tight place, such as a joint or where a limb joins the torso. Preferably, this blade housing will have an opening on its inside wall which matches up to a vacuum intake duct in the main housing of the cast saw apparatus, so the cover can direct dust into this vacuum intake.

Preferred embodiments of the invention may have an integrated vacuum duct system passing through the main housing of the cast removal apparatus, including the vacuum inlet mentioned above and a vacuum outlet. A swivel connection or other suitable connection feature may be located at the vacuum outlet to allow connection of a small flexible hose on the end of the housing's grip portion. Such a swivel is desirable as it relieves resistance of the hose which hinder the motion of other known tools that have rigid connections for a vacuum exhaust system. In embodiments of the invention that utilize an AC motor, the power cord may also be provided with a swivel at the location where it enters the housing.

Preferably, the housing of the cast removal apparatus may have a pistol grip portion set at an angle to the main housing portion such that the operator's wrist is in its natural position relative to the forearm and to the work. The operator's line of light will thus be straight down to top of the main housing portion, and in line with the saw blade. The blade may thus be guided with a pushing motion by a natural extension of the arm, while the blade drive mechanism is cutting with an efficient cutting motion as described above. In this case, the center of mass of the tool will generally be above the junction of the grip with the tool body, close to the hand. A trigger may be provided on the front of the grip portion to turn the motor on and off. A thumbwheel may, for example, be located on the side of the main housing portion to allow adjustment of variable speed settings.

The housing of the cast removal apparatus may be formed of molded plastic, reinforced with carbon fiber, permitting it to have walls that are thin and light but also strong. The interior of the walls may be lined with a suitable sound absorbing material, such as a foam or polymeric material that is engineered to absorb sounds in the frequency range of the noise produced by the motor. Also, sound and vibration absorbing panels may be provided on the exterior of the housing (e.g., as an overmold). Further, the grip portion may be separated from the main housing portion by an intervening layer of sound absorbing material (e.g., polymer), which tends to reduce fatigue of the operator.

In some preferred embodiments, the housing of the cast removal apparatus may be modular so it can be configured to use different motors, power supplies, batteries, power transmission units, and saw blades, as necessary or desired. Preferably, a modular tool can be set up optimally to cut thick or thin casts of any common material, as well as less common materials. For example, it can cut fiberglass, plastics, and wood in a more precise, controlled, and efficient manner than the known art.

In this regard, various embodiments of the present invention may employ different types of motors, including brushless DC motors, which are more efficient and more powerful for their weight than conventional motors used in prior art cast saws. This further reduces overall weight, vibration, noise, and heat, and permits the apparatus to be powered with small higher voltage batteries which plug into the back end of the main housing portion. The motor may be cooled by pulling clean air in from the rear of the body and exhausting it towards the front (i.e., near the saw blade) pushing any stray dust away from the tool and the motor.

Other features are also contemplated in various embodiments. For example, a headlight may be provided on the tool (e.g., a small LED headlight). A vacuum system specially designed for this medical application may also be provided. Known cast saws simply employ a noisy woodworking shop vacuum, which may have to be located in a closet. Preferred embodiments of the present invention employ a small vacuum which is quiet enough to be located next to the patient without frightening them.

Referring now to FIG. 1, an exemplary cast removal apparatus 10 constructed in accordance with an embodiment of the present invention is illustrated. As shown, apparatus 10 has a housing 12 having a main housing portion 14 and a grip (handle) portion 16. A motor is located inside main housing portion 14 and has a driven shaft extending therefrom in the direction of the axis of main housing portion 14. As can be seen, the grip portion 16 is oriented at an angle with respect to main housing portion 14 to allow movement of apparatus 10 along the operator's line of line by extension of the arm. In this regard, the blade 18 is aligned with the direction of grip portion 16.

In this embodiment, blade 18 has an approximately semicircular configuration and follows an orbital, galloping movement. As a result, the blade will enter and move through the cast material in an efficient fashion, and dust is cleared between the cutting teeth as they exit. As will be explained below, the blade in this case is interconnected to a wheel 20 at a location offset from the wheel's axis of rotation 22. The wheel itself is attached for rotation to the distal end of a shaft extending from a right-angle gear box 24. Right angle gear box 24 is attached to the end of the motor shaft. A trigger 26 is located on the front of grip portion 16 and can be depressed to turn on the motor, thus activating movement of blade 18.

In this embodiment, housing 12 defines an internal duct 28 (FIG. 4) that may be connected to an external vacuum system to draw away dust as it is generated by the cutting process. This internal duct thus defines an intake 30 near the location of the work. The other end of duct 28 forms an outlet for fluid communication with a suitable vacuum hose 32. Preferably, a swivel connection 34 may be provided for connecting vacuum hose 32 to facilitate movement of apparatus 10 during use. Main housing portion 14 may also define air intakes 36a and 36b allowing ingress of cooling air for the motor.

As noted above, embodiments of apparatus 10 are contemplated utilizing either battery power (e.g., having a DC motor) or power via a mains AC source (e.g., having an AC motor). The embodiment shown in FIG. 1 diagrammatically illustrates the position of a removable battery pack 38 that may be used with DC embodiments. In this example, battery pack 38 is partially inserted into a receptacle defined in the end of main housing portion 14 opposite blade 18. This provides balance that facilitates use of apparatus 10. In AC embodiments, a power cord 40 may enter the housing 12 at grip portion 16. A swivel connection 42 may be provided at the connection location to facilitate use of apparatus 10. A thumb wheel 44 located on the side of main housing portion 14 in this embodiment allows the operator to vary speed of the motor.

Figure 2:
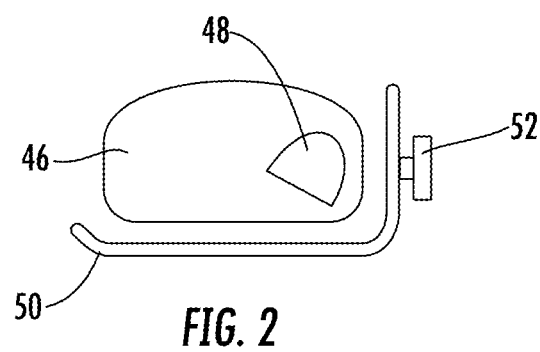
FIG. 2 shows a blade guard and foot that may preferably be used with the apparatus of FIG. 1.

Referring now to FIG. 2, a guard 46 is illustrated that may be attached to the end of main housing portion 14 to enclose much of blade 18, as well as wheel 20 and gear box 24. Preferably, guard 46 may define a slot through which a portion of blade 18 extends, or is otherwise configured not to obstruct the working portion of blade 18. As noted above, guard 46 may be formed of a clear plastic or other suitable transparent material in some preferred embodiments. Guard 46 may preferably define a vacuum intake 48 aligned with intake 30 to allow dust to be drawn away from the working area. In addition, a "foot" structure 50, attached via a locking mechanism 52, may be attached to guard 46 and/or main housing portion 14 to limit the plunge depth of blade 18 without requiring the operator to attempt to do so manually (e.g., via the operator's thumb). Locking mechanism 52 may include a screw located in a slot so that the screw can be tightened to secure the foot structure 50 in a desired position.

FIG. 3 illustrates a novel slider crank mechanism 54 that may be utilized in apparatus 10 to create the desired motion of blade 18. One skilled in the art will appreciate that some parts of mechanism 54 will be located behind others in this view, but all are shown in solid lines in FIG. 3 for purposes of illustration. In this embodiment, wheel 20 is pivotally connected at 56 to a mounting bar 58 which carries blade 18. Mounting bar 58 is attached to the distal end of a slider bar 60 that slides within a slider housing 62. Mounting bar 58 and slider bar 60 may be separate pieces (e.g., rod-shaped pieces) secured together (as by welding) or may be formed together from a single piece of stock material (e.g., flat sheet material). Slider housing 62 includes a mounting portion 64 that attaches in pivotal fashion to the inside of main housing portion 14.

Whereas slider crank mechanisms are sometimes used to convert rotational movement to reciprocating movement, it will be appreciated that mechanism 54 functions differently. As wheel 20 rotates due to operation of the motor, pivotal connection 56 orbits axis 22. This causes the toothed edge 66 of blade 18 to move in a "galloping" motion whereby successive teeth enter, move through, and then exit the kerf. In this embodiment, the orbit of pivotal connection 56 is circular, but one skilled in the art will appreciate that alternative mechanisms will often be desirable in which the orbit is more elliptical. Alternatively, or in addition, the shape of blade 18 may be modified to simulate more of an elliptical motion.

Certain additional details can be most easily explained with reference to FIG. 4, which shows aspects of the interior of housing 12 in partial cross section and diagrammatic fashion. As noted above, housing 12 is preferably formed of a light and strong material such as carbon fiber reinforced plastic. The inner surfaces of main housing portion 14 may be layered, at least in part, with a suitable sound absorbing material 68 (such as a sound absorbing foam, sound absorbing polymer, or the like), to reduce vibration and escape of sound caused by operation of motor 70. In addition, main housing portion 14 and grip portion 16 may be flexibly attached to each other and/or the connection location may also be provided with a sound absorbing material, as indicated at 72, to lessen transfer of vibration to the operator's hand.

As noted above, main housing portion 14 preferably includes air intakes 36*a-b* to allow entry of ambient air to cool the motor (as indicated by arrow 74). In this regard, motor 70 may include or be connected to a suitable fan which draws in ambient air. The air is preferably exhausted (as indicated by arrow 76) through vents positioned toward the blade end of main housing portion 14.

Figure 5A:
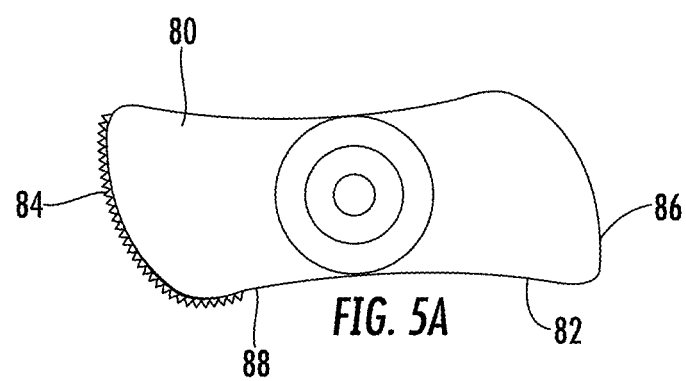
FIGS. 5A through 5C illustrate an alternative blade design that may be used with a cast removal apparatus in accordance with the present invention.
Figure 5B:
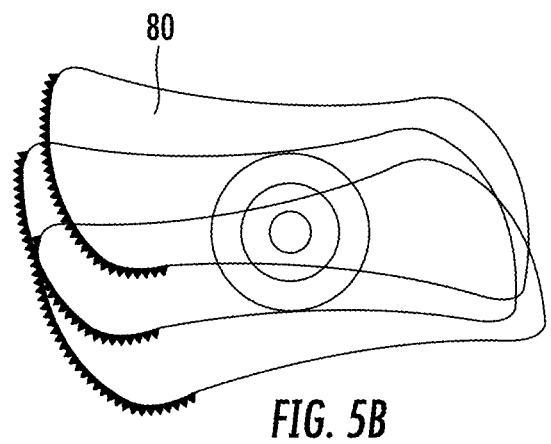
Figure 5C:
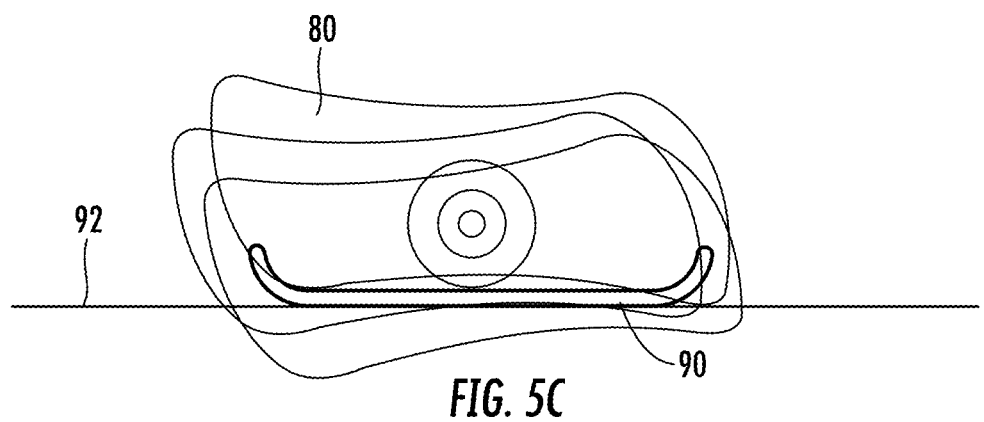

FIG. 5A illustrates an alternative configuration of a blade 80 that may be used with embodiments of the present invention. In this embodiment, blade 80 comprises a flat blade member having a generally rectangular shape. The cutting edge 82 of blade 80 includes forward and aft edge portions 84 and 86 and a bottom edge portion 88, all lined with cutting teeth (although teeth are shown on only part of cutting edge 82 for simplicity of illustration). In this embodiment, bottom edge portion 88 and its opposite top edge portion each have a recessed concave configuration. The resulting "hourglass" shape of blade 80 simulates a more elliptical, galloping cutting motion even when the driving movement is orbital described above. FIGS. 5B and 5C show blade 80 in different positions during operation to illustrate the galloping movement of the blade in preferred embodiments, which brings more teeth into contact with the cast. A guide foot 90 is also shown in FIG. 5C to limit cutting depth in relation to the surface 92 of the cast.

It will be appreciated that blades 18 or 80 can be pushed or pulled by the operator depending on the situation. Embodiments are contemplated in which the tooth pitch and "set" (i.e., divergence from vertical) is varied along the edge of the blade. Finer teeth at the location where the blade initially engages the cast facilitate beginning the cut. Teeth farther away from this initial location can be more aggressive in size and/or set.

It can thus be seen that the present invention provides a novel orthopedic cast removal apparatus. A cast removal apparatus of the present invention includes improvements over known devices in view of materials, motors, mounting, driving, blades, weight, balance, size, ergonomics, and reduction in noise and dust. While one or more preferred embodiments of the invention have been described above, it should be understood that any and all equivalent realizations of the present invention are included within the scope and spirit thereof. The embodiments depicted are presented by way of example only and are not intended as limitations upon the present invention. Thus, it should be understood by those of ordinary skill in this art that the present invention is not limited to these embodiments since modifications can be made. Therefore, it is contemplated that any and all such embodiments are included in the present invention as may fall within the scope and spirit thereof.

What is claimed is:

1. An orthopedic cast removal apparatus comprising:
   a housing having a portion that can be gripped by an operator during use;
   a motor located inside said housing;
   a blade operatively connected to and driven by said motor via a drive mechanism, said blade defining a cutting edge having cutting teeth located thereon;
   said drive mechanism having a driven element with an axis of rotation substantially orthogonal to a plane of the blade, said blade being connected to said driven element at a connection point that moves periodically around said axis of rotation;
   wherein said cutting edge of said blade engages material of the orthopedic cast in a galloping fashion;
   wherein said connection point orbits around said axis of rotation in a circular path;
   wherein said drive mechanism includes a right angle gearbox interconnecting an output shaft of said motor with said driven element;
   further comprising a slider crank mechanism and wherein said driven element is part of the slider crank mechanism;
   wherein said driven element comprises a blade mounting bar integrally attached to a slider bar; and
   wherein at least a portion of said slider bar slidably moves in a slider housing pivotally attached to said housing.

2. An orthopedic cast removal apparatus as set forth in claim 1, wherein said housing has a main housing portion containing said motor and a grip portion attached to said main housing portion.

3. An orthopedic cast removal apparatus as set forth in claim 2, wherein said blade is oriented in a plane that is parallel to an axial plane of said grip portion.

4. An orthopedic cast removal apparatus as set forth in claim 2, further comprising sound absorbing material located inside said main housing portion.

5. An orthopedic cast removal apparatus as set forth in claim 2, further comprising:
   a vacuum duct passing through said housing;
   a vacuum inlet defined in said housing in fluid communication with said vacuum duct; and
   a vacuum outlet defined in said housing for connection to a vacuum source.

6. An orthopedic cast removal apparatus as set forth in claim 5, comprising a swivel connection at which said vacuum source is connected.

7. An orthopedic cast removal apparatus as set forth in claim 1, further comprising a foot mounted to said housing to limit the plunge depth of said blade.

8. An orthopedic cast removal apparatus as set forth in claim 1, wherein said motor is a DC motor powered by at least one battery pack received in a receptacle defined in said housing.

9. An orthopedic cast removal apparatus as set forth in claim 1, wherein said motor is an AC motor.

10. An orthopedic cast removal apparatus as set forth in claim 1, wherein said cutting edge of said blade has a generally semicircular configuration.

11. An orthopedic cast removal apparatus as set forth in claim 1, wherein said cutting edge of said blade has a forward edge portion, an aft edge portion, and a concave bottom edge portion.

\* \* \* \* \*